United States Patent
Kusuhara (10) Patent No.: US 10,019,783 B2
(45) Date of Patent: Jul. 10, 2018

(54) TEST PIECE ANALYZING APPARATUS AND TEST PIECE ANALYZING METHOD

(71) Applicant: Sysmex Corporation, Kobe-shi, Hyogo (JP)

(72) Inventor: Takashi Kusuhara, Tokyo (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 20 days.

(21) Appl. No.: 15/287,195

(22) Filed: Oct. 6, 2016

(65) Prior Publication Data
US 2017/0103543 A1    Apr. 13, 2017

(30) Foreign Application Priority Data
Oct. 9, 2015   (JP) ................ 2015-201502

(51) Int. Cl.
| | | |
|---|---|---|
| G06T 7/40 | (2017.01) | |
| G01N 21/25 | (2006.01) | |
| G06T 5/00 | (2006.01) | |
| G01N 21/84 | (2006.01) | |

(52) U.S. Cl.
CPC .............. *G06T 5/00* (2013.01); *G01N 21/25* (2013.01); *G01N 21/8483* (2013.01); *G06T 2207/10016* (2013.01); *G06T 2207/10024* (2013.01); *G06T 2207/20221* (2013.01)

(58) Field of Classification Search
CPC .................. G01N 35/10; G01N 33/84; G01N 2035/1062; G01N 35/00; G01N 33/487
See application file for complete search history.

(56) References Cited

U.S. PATENT DOCUMENTS

| | | | |
|---|---|---|---|
| 2008/0019596 A1 | 1/2008 | Seher et al. | |
| 2013/0172698 A1* | 7/2013 | Reynolds | A61B 5/14532 600/316 |
| 2014/0028857 A1* | 1/2014 | Jasperse | G01N 21/8483 348/169 |
| 2015/0031135 A1 | 1/2015 | Zimmerle et al. | |
| 2015/0369827 A1* | 12/2015 | Zimmerle | G01N 33/728 436/97 |

(Continued)

FOREIGN PATENT DOCUMENTS

| | | |
|---|---|---|
| EP | 1 801 568 A1 | 6/2007 |
| EP | 2 385 369 A1 | 11/2011 |
| JP | 2005-090969 A | 4/2005 |

OTHER PUBLICATIONS

Blicharz, T.M. et al., "Use of Colorilnetric Test Strips for Monitoring the Effect of He1nodialysis on Salivary Nitrite and Uric Acid in Patients With End-Stage Renal Disease:A Proof of Principle", *Clinical Chemistry*, vol. 54, No. 9, Jan. 1, 2008, pp. 1473-1480.

(Continued)

*Primary Examiner* — Bobbak Safaipour
(74) *Attorney, Agent, or Firm* — Brinks Gilson & Lione (57) ABSTRACT

A test piece analyzer and test piece analyzing method which is compact and capable of analyzing a test piece even when mounted obliquely is provided. The test piece analyzer is configured by a test piece holder 11 that includes a mounting part MP for mounting a test piece provided with reagent pads, and an imaging unit 20, wherein the imaging unit 20 is configured to sequentially image the test piece along the longitudinal direction of the mounting part.

15 Claims, 9 Drawing Sheets

(56) References Cited

U.S. PATENT DOCUMENTS

2016/0048739 A1\* 2/2016 Burg .................... G01J 1/4204
                                                          382/128
2017/0098137 A1\* 4/2017 Burg .................... G06K 9/6202
2017/0102402 A1\* 4/2017 Kusuhara ............. G01N 33/493
2017/0160297 A1\* 6/2017 Galano ............ G01N 35/00029

OTHER PUBLICATIONS

"Epson Perfection 3490/3590 Photo", *Epson*, Aug. 1, 2005, 4 pages.

\* cited by examiner

TEST PIECE ANALYZING APPARATUS AND TEST PIECE ANALYZING METHOD

RELATED APPLICATIONS

This application claims priority from prior Japanese Patent Application No. 2015-201502, filed on Oct. 9, 2015, entitled "Test Piece Analysis Device And Test Piece Analysis Method", the entire content of which is incorporated herein by reference.

BACKGROUND OF THE INVENTION

1. Field of the Invention

The invention relates to a test piece analyzing apparatus and test piece analyzing method.

2. Description of the Related Art

Component analysis has been performed on liquid samples using a test piece provided with a reagent pad in the fields of clinical examinations, food analysis, and other fields. For example, in clinical examinations using urine as liquid samples, concentration analyses are performed for sugar, protein, occult blood and the like using a flat rod-like test piece (multi test piece) provided with a plurality of types of reagent pads by measuring the degree of coloration of each test pad when urine has been absorbed by the reagent pad. Although the degree of coloration of the reagent pad also can be measured visually, a test piece analyzer may be used to efficiently perform high precision measurements.

Japanese Patent Application Publication No. 2005-90969 discloses an example of a conventional test piece analyzer below. Specifically discloses is a test piece analyzer provided with an analyzing part that includes a reflective optical system configured by an image sensor, lens, and reflective light source, and a test piece conveying device that conveys the test piece to a predetermined position by intermittent actuation of a plurality of mounting parts on which a test piece is mounted. In this test piece analyzer, the analyzing part is rotatably connected to the test piece conveying part, so that the analyzer can be made more compact by folding the analyzing part when not in use.

SUMMARY OF THE INVENTION

The test piece analyzer disclosed in Japanese Patent Application Publication No. 2005-90969 mentioned above is provided with a line sensor as the image sensor, and measures the degree of coloration of the reagent pad by performing image processing on a one-dimensional image (a one-dimensional image in the longitudinal direction of the test piece) obtained by imaging the test piece by the line sensor. The line sensor is a sensor in which a one-dimensional image is captured by linearly arrayed imaging elements.

A problem arises with such test piece analyzers in that the apparatus becomes enlarged and difficult to make more compact due to the necessity of maintaining the distance between the test piece and the line sensor when capturing the image of the entire test piece at one time. Consider that although it is possible to shorten the distance between test piece and line sensor if using a line sensor of approximately the same length as the test piece or longer, this is unrealistic from a cost perspective.

A conventional test piece analyzer is designed so that the width of the mounting part of the test piece analyzer on which the test piece is mounted is substantially the same as the width of the test piece, and when an operator mounts a test piece on the mounting part, the longitudinal direction of the test piece substantially matches the longitudinal direction of the line sensor. However, in a conventional test piece analyzer the operator must perform the work of mounting the test piece on the mounting part paying attention until the test is completed because the width of the mounting part is substantially the same as the width of the test piece. From the perspective of ease of work of the operator, it is desirable that the test piece analyzer is capable of performing analysis even though the test piece is inclined.

In view of this information, an object of the invention is to provide a test piece analyzer and test piece analyzing method that is compact and capable of performing analysis even when the test piece is mounted inclined.

To solve these problems, the test piece analyzer of the invention provides, in a test piece analyzer (1) that analyzes a test piece using a captured image of the test piece (TP) provided with reagent pads (PD), a test piece holder (11) including a mounting part (MP) for mounting the test piece, an imaging unit (20) configured so that the width of the imaging area is greater than the width of the mounting part in the lateral direction, wherein the imaging unit sequentially images the test piece along the longitudinal direction of the mounting part.

The test piece analyzing method of the invention analyzes a test piece using an image obtained by imaging the test piece (TP) provided with reagent pads (PD). The method sequentially images the test piece mounted on the mounting part along the longitudinal direction of the mounting part by an imaging unit (2) configured so that the width of the imaging area is greater than the width of the mounting part (MP).

According to the invention, there is an effect of making the analyzer more compact by making it possible to analyze a test piece mounted obliquely.

BRIEF DESCRIPTION OF THE DRAWINGS

FIG. 8 (A)-8(F) illustrate the image processing performed by the test piece analyzer of the embodiment of the invention;

DETAILED DESCRIPTION OF THE PREFERRED EMBODIMENTS

The test piece analyzer and test piece analyzing method of the embodiments of the invention are described in detail below referring to the drawings. In the following description, the positional relationships of every part are described while referring to the XYZ orthogonal coordinate system set in the drawings as necessary. The origin point of the XYZ orthogonal coordinate system shown in each drawing is not fixed and may change as appropriate for the convenience of the description.

Figure 1:
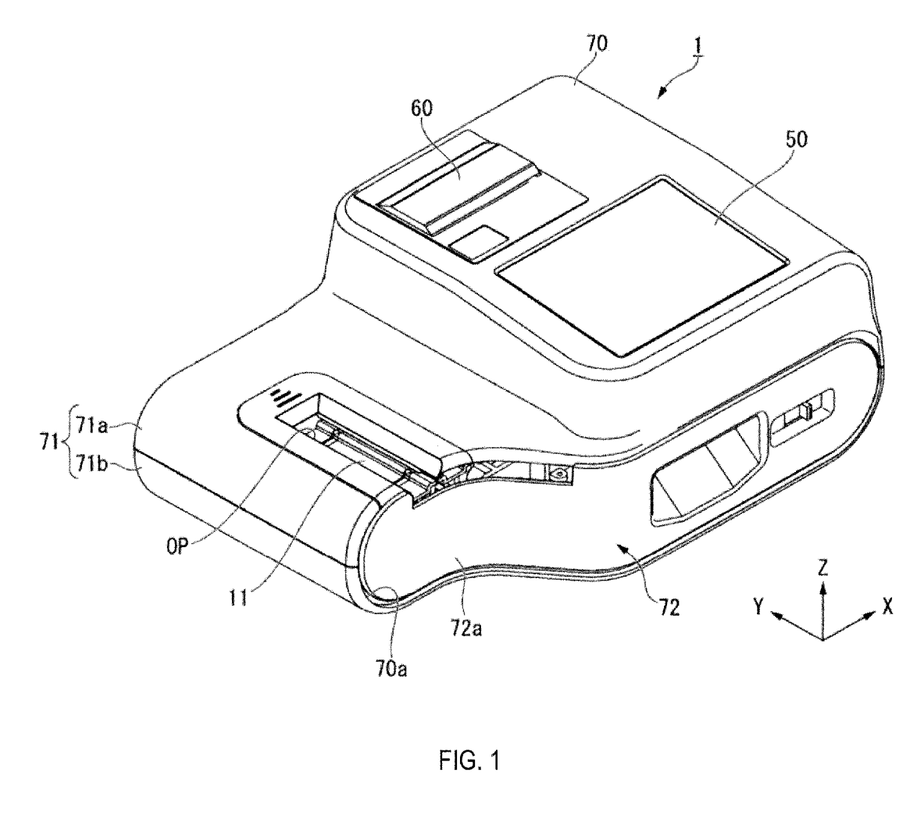
FIG. 1 is a perspective view showing the exterior of the test piece analyzer of an embodiment of the invention.
Figure 2:
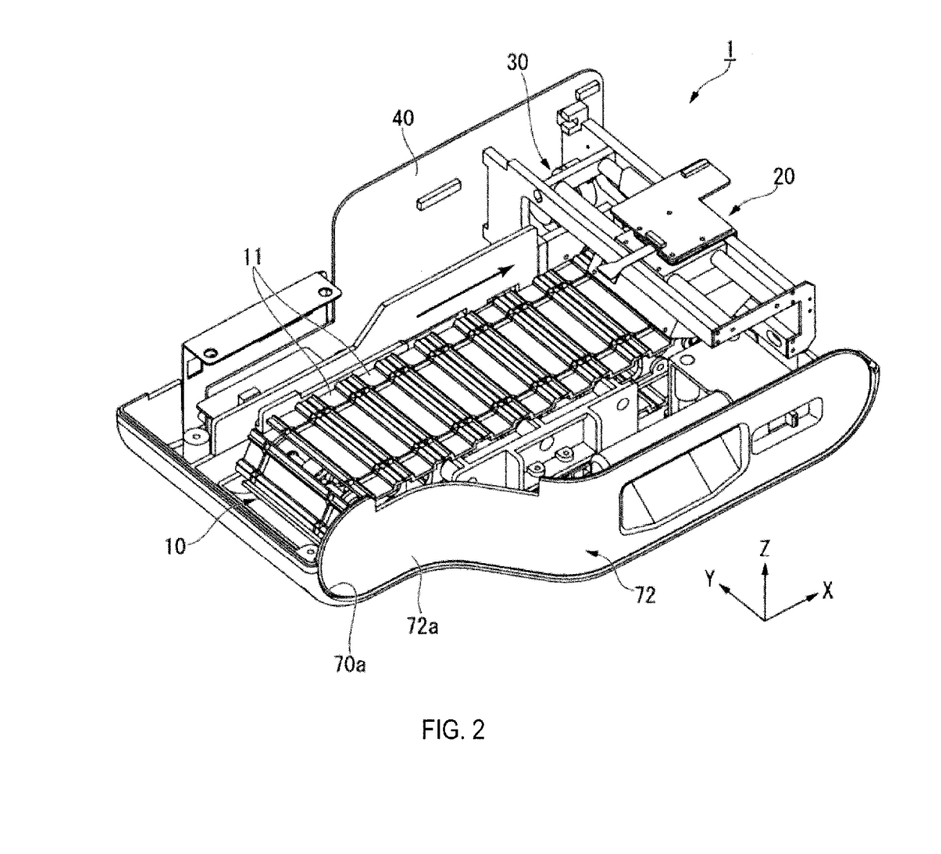
FIG. 2 is a perspective view showing the interior structure of the test piece analyzer of the embodiment of the invention.
Figure 3:
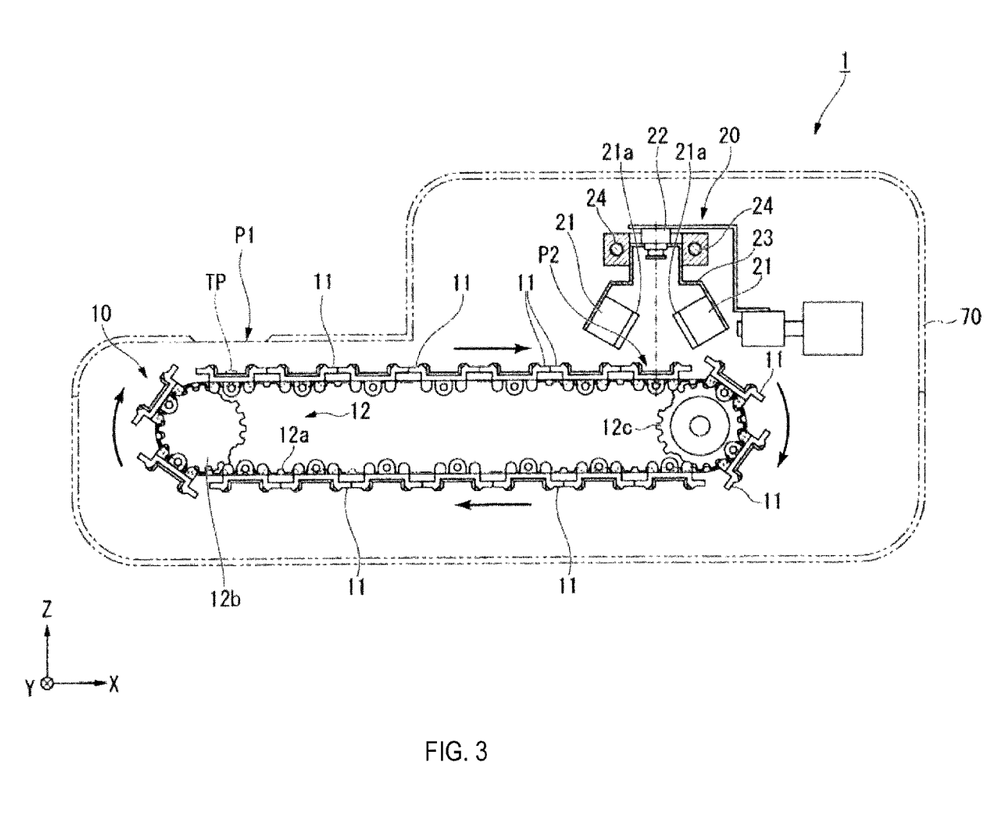
FIG. 3 is a side view schematically showing the interior structure of the test piece analyzer of the embodiment of the invention.

FIG. 1 is a perspective view showing the exterior of the test piece analyzer of an embodiment of the invention. FIG. 2 is a perspective view showing the interior structure of the test piece analyzer of the embodiment of the invention. FIG. 3 is a side view schematically showing the interior structure of the test piece analyzer of the embodiment of the invention. The XYZ orthogonal coordinate system shown in FIG. 1 through FIG. 3 is has the direction (second direction) in which the X axis is along the transport direction of the test piece TP (described later), the direction (first direction) in which the Y axis is along the transport direction of the imaging unit 20 (described later), and the Z axis direction set to be mutually perpendicular.

As shown in FIG. 1 through FIG. 3, the test piece analyzer 1 of the embodiment includes a transport unit 10, imaging unit 20, drive part 30, main board 40, display part 50, printing part 60, and housing 70. The test piece analyzer 1 images the test piece that has been transported by the transport unit 10 via the imaging unit 20, analyzes the test piece TP using the obtained image, displays the analysis result on the display part 50 or prints the analysis results via the printing part 60. In this embodiment, the liquid sample to be the object of analysis is urine.

Figure 4:
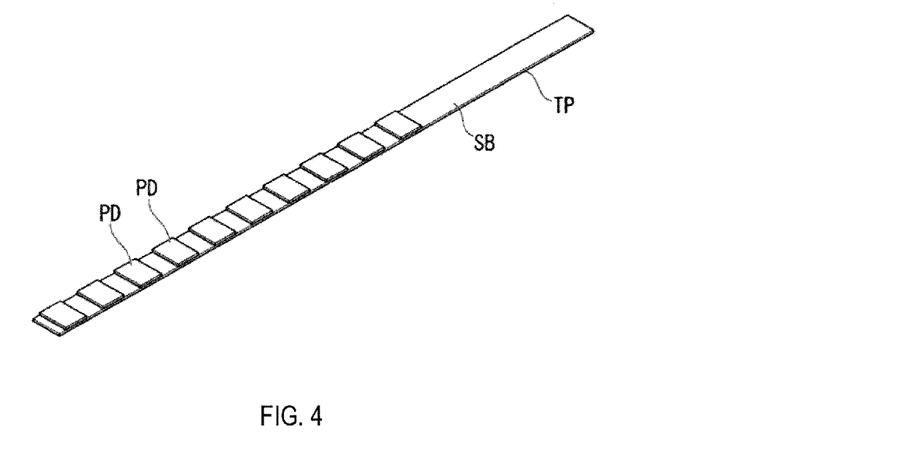
FIG. 4 is a perspective view showing an example of a test piece used by the test piece analyzer of the embodiment of the invention.

The test piece TP used in the test piece analyzer 1 is briefly described below. FIG. 4 is a perspective view showing an example of a test piece used by the test piece analyzer of the embodiment of the invention. As shown in FIG. 4, the test piece TP is a so-called multi test piece that has a flat rod-like substrate SB, and a plurality of reagent pads PD formed on the one surface of the substrate SB. The reagent pads PD absorb the liquid sample (for example, urine) that is the object of analysis, and colors in accordance with the composition of the liquid sample.

Figure 5:
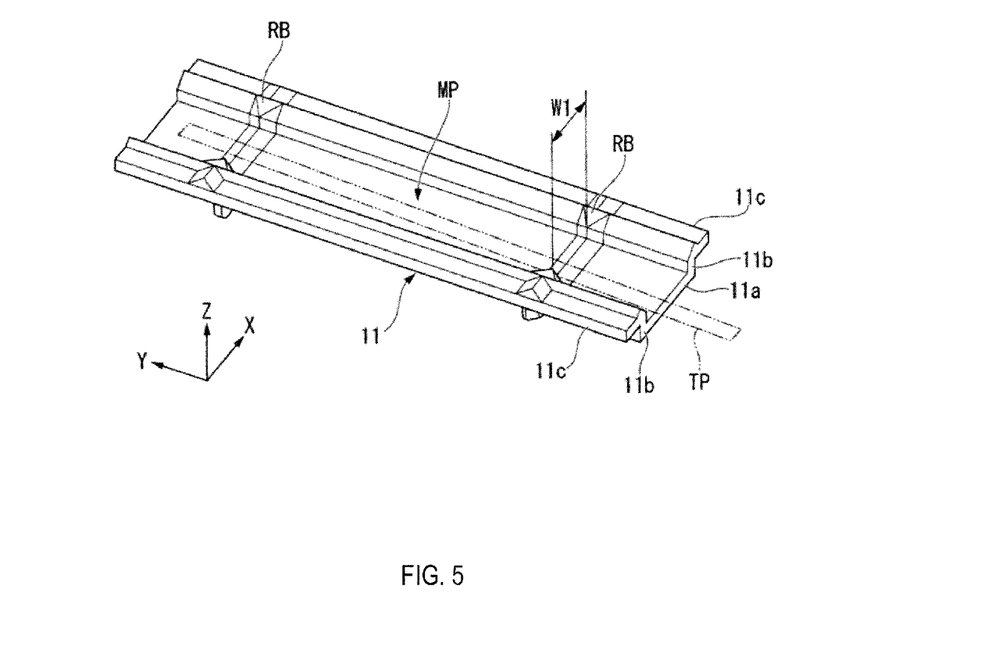
FIG. 5 is a perspective view showing the test piece holder of the embodiment of the invention.

The transport unit 10 includes a plurality of test piece holders 11 for mounting the test piece, and a transport device 12 for transporting the test piece holders, wherein the test piece TP mounted on the test piece holder 11 is transported in the X direction, as shown in FIG. 2 and FIG. 3. FIG. 5 is a perspective view showing the test piece holder of the embodiment of the invention. As shown in FIG. 5, the test piece holder 11 includes, in the plane view, a rectangular bottom plate 11a, side plates 11b erected on bilateral edges of the bottom plate 11a, and extension plates 11c extending outward from the top edges of bilateral edges 11b, respectively.

As shown in FIG. 5, a pair of rib-like protrusions RB also reformed on the test piece holder 11 in the space in the lengthwise direction (Y direction) of the test piece holder 11. The rib-like protrusions RB are provided to prevent the test piece TP from sticking to the test piece holder 11. The test piece TP also is arranged on the rib-like protrusions RB without touching the bottom plate 11a of the test piece holder 11, as shown in the drawing.

The test piece TP is mounted on the mounting part MP in the area between the side plates 11b of the test piece holder 11. Therefore, the width W1 of the mounting part MP is preferably larger than the width of the test piece TP, so that the test piece TP can be mounted on the test piece holder 11 even when the test piece TP is in an inclined condition relative to the lengthwise direction (Y direction) of the test piece holder 11 as shown in FIG. 5. In this way the work of mounting the test piece TP on the test piece holder 11 can be easily accomplished. The width W1 of the mounting part MP also preferably does not exceed double the width of the test piece TP. If the width W1 of the mounting part MP is too large, it may cause the erroneous mounting of a plurality of test pieces TP. Although the structural material of the test piece holder 11 is not specifically limited, the test piece holder 11 is preferably constructed of synthetic resin. In the image processing step (described later), it is preferable that coloration is a dark color to heighten the contrast with the test piece TP and ensure processing.

The transport device 12 includes an endless belt 12a, pulley 12b and pulley 12c. The endless belt 12a is a band-like body (or belt-like member) formed in an annular shape. A plurality of test piece holders 11 are attached independently of each other to the endless belt 12a. Therefore, the adjacent test piece holders 11 can be arranged in mutual proximity or arranged separated from one another, as shown in FIG. 3. The pulleys 12b and 12c are provided with a spacing in the X direction. Since the endless belt 12a is looped around the pulleys 12b and 12c, the endless belt 12a circulates when the pulley 12c rotates, and the pulley 12b also rotates therewith.

As shown in FIG. 3, the mounting position P1 (first position) where the test piece TP is mounted on the test piece holder 11, and the imaging position P2 (second position) where the test piece TP is imaged by the imaging unit 20 are separated by a predetermined distance in the X direction. The test piece TP seated at the mounting position P1 in the test piece holder 11 is transported to the imaging position P2 by the circulatory travel of the endless belt 12a. The time during which the test piece holder 11 moves from mounting position P1 to the imaging position P2 is set so that the reagent pad PD of the test piece TP and the components of the liquid sample will react neither excessively of deficiently, and suitably color the reagent pad PD.

The imaging unit 20 is provided with a pair of light sources 21, an imaging element 22, and support 23, and is configured to be movable in the Y direction along a pair of guide rails 24 extending in the Y direction above the imaging position P2 (+Z side). The light sources 21 and 21 irradiate the test piece TP that has been transported to the imaging position P2 by the transport unit 10. The light sources 21 and 21 are respectively arranged obliquely above the imaging position P2, so as to uniformly irradiate the test piece TP and avoiding as much as possible shadowing of the test piece TP by the test piece holder 11 by irradiating the test piece TP obliquely downward from the +X side and −X side.

The light sources 21 and 21 are provided with light emitting elements such as, for example, a light emitting diode (LED) or laser diode (LD). Since the degree of coloration of the reagent pad PD provided on the test piece TP is measured by the test piece analyzer 1, it is preferable that the light emitting element provided in the light sources 21 and 21 is, for example, a light emitting element that emits white light. One or more light emitting element may be provided in each of the light sources 21 and 21. The light sources 21 and 21 are respectively provided with a diffusion panel 21a to equalize the illumination light output from the light sources 21 and 21.

The imaging element 22 is an imaging element (area sensor) that captures the image (two-dimensional image) of the test piece TP that has been transported to the imaging position P2 by the transport unit 10. The imaging element 22 is arranged above (+Z direction) the imaging position P2 with the imaging surface facing the bottom side (−Z side).

The size of the imaging area of the imaging element 22 is set to a size to image part of the test piece TP disposed at the imaging position P2. This arrangement realizes a compact test piece analyzer 1 by reducing as much as possible the distance between the test piece TP and the imaging element 22.

Specifically, the length in the Y direction of the imaging area of the imaging element 22 is set smaller than the length of the test piece TP, for example, a length of about ¼ the length of the test piece TP. The width in the X direction of the imaging area of the imaging element 22 is set larger than the width W1 (refer to FIG. 5) of the mounting part MP of the test piece holder 11. As shown in FIG. 5, this arrangement obtains images of the entire test piece TP even when the test piece TP is inclined relative to the length direction (Y direction) of the test piece holder 11.

The imaging element 22, for example, is set at approximately 40 mm from the top surface of the bottom plate 11a of the test piece holder 11 disposed at the imaging position P2. The length in the Y direction and the width in the X direction of the imaging area of the imaging element 22, for example, are set at approximately 30 mm. The numeric values given above are examples only and may be suitably modified according to the specifications of the test piece analyzer 1.

The imaging element 22 is a two-dimensional RGB color image sensor (area sensor) such as a CCD (charge-coupled device) image sensor, CMOS (complementary metal oxide semiconductor) image sensor and the like. The imaging element 22 also may be a two-dimensional monochrome image sensor combined with an RGB filter.

The support 23 integratedly supports the light sources 21 and 21, and the imaging element 22. The relative positional relationships of the light sources 21 and 21, and the imaging element 22 are unchanged when the light sources 21 and 21 and the imaging element 22 are integratedly supported by the support 23. Therefore, the illumination conditions when the imaging element 22 images the test piece TP are unchanged (or substantially unchanged) even when the imaging unit 20 moves in the Y direction along the pair of guide rails 24 and 24.

The drive part 30 includes a motor (for example, a stepping motor), and drives the transport unit 10 and the imaging unit 20. Specifically, the drive part 30 includes a motor M1 (refer to FIG. 6) to rotationally drive the pulley 12c provided in the transport unit 10, and the endless belt 12a circulates when the motor M1 is actuated. Although details are provided later, the drive part 30 also intermittently rotates the pulley 12c, and intermittently moves the test piece holder 11 mounted on the endless belt 12a. The drive part 30 also includes a motor M2 (refer to FIG. 6) used by the imaging unit 20, and the imaging unit 20 moves reciprocatingly in the Y direction along the pair of guide rails 24 and 24 when the motor M2 is actuated.

The main board 40 is a substrate for mounting a CPU (central processing unit), volatile memory such as RAM (random access memory), nonvolatile memory such as ROM (read only memory), and other electronic components. Control of the operation of the test piece analyzer 1 and processing to analyze the test piece TP are performed by the circuits configuring the electronic components mounted on the main board 40. The structure of the control system of the test piece analyzer 1 is described later.

The display part 50 includes, for example, a touch panel type liquid crystal display device that has a display function and an operation function to display analysis results of the test piece TP and images of the test piece TP, as well as an operation guide specifying the timing for mounting the test piece TP in the test piece holder 11, and inputting operation information according to the operation when performing an operation on the display screen of the liquid crystal display device. The printing part 60 includes, for example, a thermal printer, to print the analysis results of the test piece TP when a print instruction is input through the operation on the display screen of the liquid crystal display device of the display part 50.

The housing 70 has an exterior part 71 and a pull-out part 72. The exterior part 71 is configured by a top panel 71a and a bottom panel 71b, and the previously mentioned transport unit 10, imaging unit 20, drive part 30, and main board 40 and the like are accommodated in the interior space between the top panel 71a and the bottom panel 72b. A pull-out port 70a for pulling out the transport unit 10 is formed in the side part (side part on the −Y side) of the exterior part 71.

A mounting port OP, that is, and opening that exposes at least part of the test piece holder 11 at the mounting position P1, is formed in the top panel 71a of the exterior part 71. The shape of the mounting port OP is a slit shape extending along the Y direction. Specifically, the mounting port OP is formed to expose at least part of the top surface (refer to FIG. 5) of the bottom plate 11a of the test piece holder 11 at the mounting position P1.

The width (dimension in the X direction) of the mounting port OP is formed larger than the width of the test piece TP. For example, the width of the mounting port OP is set to double the width of the test piece TP. The test piece TP can be mounted on the test piece holder 11 even when the orientation of the test piece TP is inclined relative to the Y direction (refer to FIG. 5) in plan view since the width of the mounting port OP is larger than the width of the test piece TP. In this way the work of mounting the test piece TP on the test piece holder 11 can be easily accomplished.

The pull-out part 72 includes a support member (not shown in the drawing) that supports the transport unit 10, and the exterior panel 72a that covers substantially the entirety of the pull-out port 70a. The pull-out part 72 is a separate from the exterior part 71, and is accommodated within the exterior part 71 when the transport unit 10 is housed in the exterior part 71. The pull-out part 72 and the transport unit 10 also are freely and integratedly placed in and taken out of the exterior part 71 through the pull-out port 70a.

Figure 6:
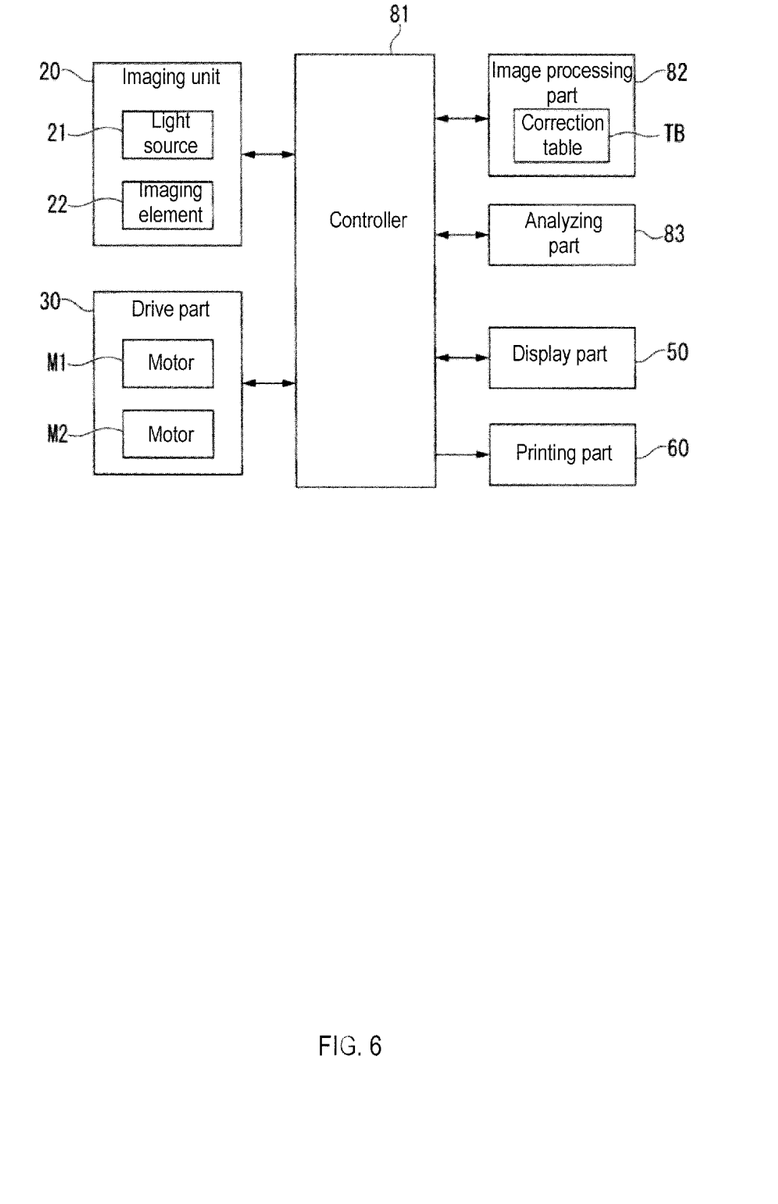
FIG. 6 is a block diagram showing the structure of the control system of the test piece analyzer of the embodiment of the invention.

FIG. 6 is a block diagram showing the structure of the control system of the test piece analyzer of the embodiment of the invention. In FIG. 6, the block diagram corresponds to the structures shown in FIGS. 1 through 3 and is denoted by identical reference numbers. As shown in FIG. 6, the test piece analyzer 1 is provided with a controller 81, image processing part 82, and analyzing part 83 in addition to the imaging unit 20, drive part 30, display part 50, and printing part 60. The motor M1 that drives the transport unit 10 (omitted in FIG. 6), and the motor M2 that moves the imaging unit 20 in the Y direction are provided in the drive part 30.

The controller 81, image processing part 82, and analyzing part 83 are realized by having the CPU (not shown in the drawing) provided on the previously mentioned main board 40 execute programs to realize the various functions. That is, the controller 81, image processing part 82, and analyzing part 83 are realized by the cooperating hardware and software resources. The controller 81, image processing part 82, and analyzing part 83 also may be realized by dedicated hardware.

The controller 81 generally has overall control of the operations of the test piece analyzer 1. Specifically, the controller 81 controls the motor M1 provided in the drive part 30 to drive the transport unit 10, and controls the motor M1 provided in the drive part 30 to move the imaging unit 20 in the Y direction. The controller 81 also controls the emission and non-emission of the light sources 21 provided in the imaging unit 20, and controls the imaging element 22 provided in the imaging unit 20 to capture an image of the test piece TP. The controller 81 also controls the start timing of the processes performed by the image processing part 82 and the analyzing part 83. The controller 81 also performs display controls of the display part 50, and printing controls of the printing part 60.

The image processing part 82 performs image processing on the plurality of images (hereinafter referred to as "partial images") obtained by imaging the test piece TP via the imaging element 22 while changing the position in the Y direction. Specifically, the image processing part 82 performs the processes (1) through (3) below.

(1) Correction process
(2) Combining process
(3) Extraction process

The "correction process" above is a process for correcting the brightness of the partial images using a brightness correction table (a table for correcting irregular brightness within the imaging area of the imaging element 22) provided in the image processing part 82. The brightness within the imaging area of the imaging element 22 becomes irregular due to the optical system (light sources 21, lenses not shown in the drawings and the like), for example, brightness may be different in the center part and the periphery. The "correction process" above is performed to correct this brightness irregularity, and improve the measurement accuracy of the degree of coloration of the reagent pads PD provided on the test piece TP.

As described above, the illumination conditions when the test piece TP is imaged by the imaging element 22 are unchanged (or substantially unchanged) even when the imaging unit 20 is moved in the Y direction along the pair of guide rails 24. Therefore, the "correction process" relative to the plurality of partial images is performed using a single brightness correction table TB. The brightness correction table TB also is a two-dimensional table that associates the amount of brightness correction, and the position in the Y direction and X direction within the imaging area of the imaging element 22. The brightness correction table TB is prepared, for example, by installing a reference plate (for example, a white color reference plate) in the test piece analyzer 1 before shipment, and using the images obtained by imaging this reference plate via element 22.

The "combining process" above is a process for obtaining an image that includes the entire test piece TP (referred to as "composite image" below) by combining the plurality of partial images. The partial images are images obtained by imaging parts of the test piece TP, and the test piece TP cannot be analyzed by the analyzing part 83 using the partial images alone. The "combining process" is performed to enable analysis of the test piece TP by the analyzing part 83.

The "extraction process" above is a process for extracting the image of the test piece TP (referred to as "extraction image" below) from the composite image obtained through the "combining process". That is, the "extraction process" is a process that extracts only the image of the test piece TP contained in the composite image, and eliminates the image that is not the test piece TP (for example, the image of the test piece holder 11). This process is performed to enable analysis of the test piece TP by the analyzing part 83 without performing complex image processing even when the test piece TP is inclined relative to the length direction (Y direction) of the test piece holder 11.

The analyzing part 83 measures the degree of coloration of the reagent pad PD provided on the test piece TP using the image previously subjected to each of the above processes (correction process, combining process, extraction process) by the image processing part 82, and performs concentration analyses of the sugar, protein, and occult blood in the urine. Detailed description of the analyses performed by the analyzing part 83 is omitted since it is well known.

The operation of the test piece analyzer 1 of the above configuration is described below. When the power supply of the test piece analyzer 1 is switched on, the controller 81 controls the motor M1 of the drive part 30 to intermittently rotate the pulley 12c provided in the transport unit 10. In this way the endless belt 12a provided in the transport unit 10 intermittently circulates in the arrow direction shown in FIG. 3, and intermittently moves the test piece holder 11 mounted on the endless belt 12a.

A operator performed the work of immersing the test piece TP in the urine liquid sample, then mounts the test piece TP (that is, the test piece TP that has absorbed urine in the reagent pad PD) on the test piece holder 11 disposed mounting position P1 through the mounting port OP. Then the test piece TP mounted on the test piece holder 11 is transported in the +X direction by moving the test piece holder 11. The test piece TP also is transported with the reagent pad PD facing upward (+Z side), and the reagent pad PD is colored through the reaction of the urine components and the reagent pad PD of the test piece TP.

When the test piece 3 holder 11 with the mounted test piece TP is transported to the imaging position P2, the motor M2 of the drive part 30, and light sources 21 of the imaging unit 20, and imaging element 22 are controlled by the controller 81 as shown in FIG. 6. As the imaging unit 20 is moved in the Y direction along the guide rails 24 and 24, the operation of imaging the test piece TP is performed by the imaging element 22, all under the control of the controller 81.

Figure 7:
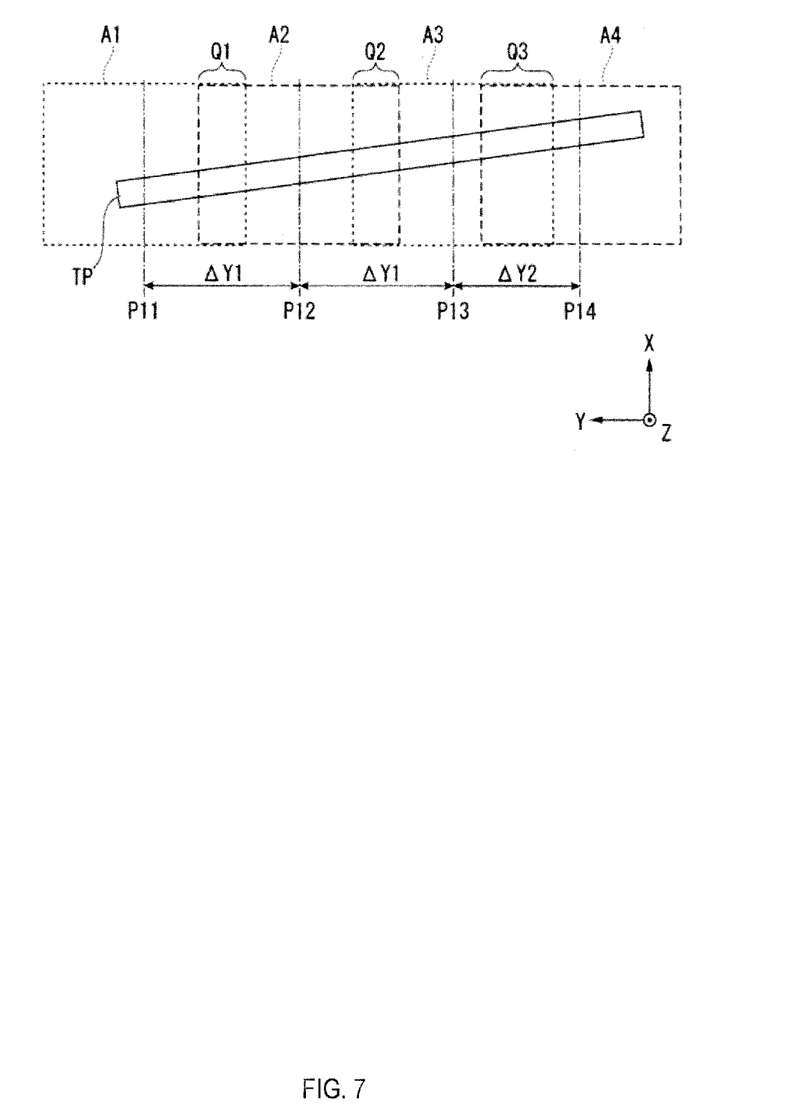
FIG. 7 illustrates the situation of imaging the test piece by the test piece analyzer of the embodiment of the invention.

FIG. 7 illustrates the situation of imaging the test piece by the test piece analyzer of the embodiment of the invention. When the operation of imaging the test piece TP starts, the imaging unit 20 that is first positioned at the home position and is moved in the Y direction to the first imaging position P11 shown in FIG. 7 by the control of the controller 81. The home position also is a reference position of the imaging unit 20, and is set, for example, at the end position on the +Y side of the movement range of the imaging unit 20.

When the imaging unit 20 is positioned at the imaging position P11, the light sources 21 of the imaging unit 20 emit light, and a partial image (specifically, the image within the imaging range A1 shown in FIG. 7) of the test piece TP is captured through the control of the controller 81. When the imaging at imaging position P11 is completed, the light sources 21 of the imaging unit 20 are shut off, and the imaging unit 20 disposed at the imaging position P11 is moved in the −Y direction to the imaging position P12 shown in FIG. 7 through the control of the controller 81.

When the imaging unit 20 is positioned at the imaging position P12, the light sources 21 of the imaging unit 20 emit light, and another partial image (specifically, the image within the imaging range A2 shown in FIG. 7) of the test piece TP is captured through the control of the controller 81. When the imaging at imaging position P12 is completed, the light sources 21 of the imaging unit 20 are shut off, and the imaging unit 20 disposed at the imaging position P12 is moved in the −Y direction to the imaging position P13 shown in FIG. 7 through the control of the controller 81.

When the imaging unit 20 is positioned at the imaging position P13, the light sources 21 of the imaging unit 20 emit light, and another partial image (specifically, the image within the imaging range A3 shown in FIG. 7) of the test piece TP is captured through the control of the controller 81. When the imaging at imaging position P13 is completed, the light sources 21 of the imaging unit 20 are shut off, and the imaging unit 20 disposed at the imaging position P13 is moved in the −Y direction to the imaging position P14 shown in FIG. 7 through the control of the controller 81.

When the imaging unit 20 is positioned at the imaging position P14, the light sources 21 of the imaging unit 20 emit light, and another partial image (specifically, the image within the imaging range A4 shown in FIG. 7) of the test piece TP is captured through the control of the controller 81. When the imaging at imaging position P14 is completed, the light sources 21 of the imaging unit 20 are shut off, and the imaging unit 20 disposed at the imaging position P14 is moved in the +Y direction to the home position (not shown in the drawing) through the control of the controller 81. In this way the test piece TP is imaged. The light sources 21 of the imaging unit 20 also may emit light from the start to the completion of the imaging of the test piece TP.

As shown in FIG. 7, the distance separating imaging position P11 and imaging position P12 is set at $\Delta Y1$ to create an overlap part Q1 of the imaging area A1 and imaging area A2. The distance separating imaging position P12 and imaging position P13 also is set at $\Delta Y1$ to create an overlap part Q2 of the imaging area A2 and imaging area A3. The width of the overlap parts Q1 and Q2 also are identical.

In contrast, the distance $\Delta Y2$ separating imaging point P13 and imaging point P14 is set to a distance shorter than the distance $\Delta Y1$ from the relationships of making the test piece analyzer 1 compact. In this way the width of the overlap part Q3 is set larger than the width of the overlap parts Q1 and Q2 although the overlap part Q3 is created by the overlapping of the imaging area A3 and imaging area A4. Although described in detail later, the image processing part 82 performs the previously mentioned combining process in consideration of the different width of the overlap part Q3 relative to the overlap parts Q1 and Q2. The creation of the overlap parts Q1 through Q3 also is to avoid creating a non-imaged part of the test piece TP due to the partial imaging of the test piece TP by the imaging element 22.

Figure 8:
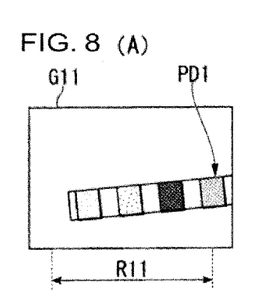
Figure 8C:
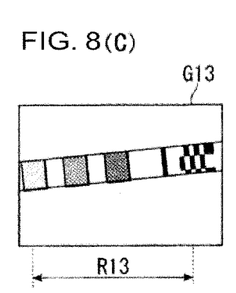

When the imaging of the test piece TP is completed, the partial images made by the imaging element 22 are input to the image processing part 82 through the controller 81 as shown in FIG. 6, and image processing (previously mentioned correction process, combining process, extraction process) is performed on the partial images. FIG. 8 illustrates the image processing performed by the test piece analyzer of the embodiment of the invention. FIG. 8 (A) through (D) respectively show examples of partial images G11 through G14 captured at imaging positions P11 through P14 shown in FIG. 7. FIG. 8 (E) shows the composite image G20 obtained by combining the partial images G11 through G14. FIG. 8 (F) shows the extraction image G30 extracted from the composite image G20.

Figure 9:
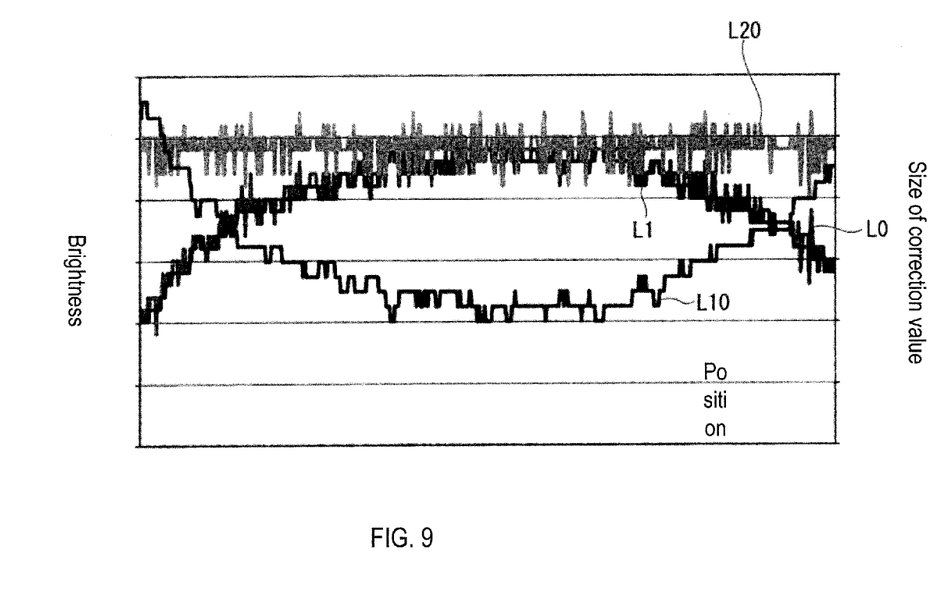
FIG. 9 illustrates the principle of the correction process performed by the test piece analyzer of the embodiment of the invention.

When the image processing starts, the image processing part 82 first performs the correction process on each of the partial images G11 through G14 shown in FIG. 8 (A) through (D). FIG. 9 illustrates the principle of the correction process performed by the test piece analyzer of the embodiment of the invention. The horizontal axis of the graph shown in FIG. 9 represents the position (position in the X direction or position in the Y direction) within the imaging area of the imaging element 22. The vertical axis of the graph shown in FIG. 9 represents the brightness or the size of the correction value.

The curve labeled L0 in FIG. 9 is a curve representing an example of the brightness distribution of the image obtained by imaging the reference plate (that is, the reference plate used to create the brightness correction table TB before the test piece analyzer 1 is shipped). FIG. 9 shows a unidimensional brightness distribution (for example, brightness distribution in the Y direction) of the image obtained by imaging the reference plate to simplify comprehension.

The curve labeled L1 in FIG. 9 is obtained by calculating the moving average of the curve L0 to eliminate the influence of noise. The curve L1 also may be referred to as a curve representing the brightness distribution within the imaging field of view of the imaging element 22. When referring to the curve L1, it can be understood that the brightness of the imaging field of view of the imaging element 22 has a distribution that is highest in the center area and lowest at the periphery. The brightness distribution of the imaging field of view of the imaging element 22 is substantially the same as that of curve L1 in both the X direction and Y direction.

The curve labeled L10 in FIG. 9 is an example of the correction values of the brightness correction table TB created using the curve L1. As shown in FIG. 9, the correction values of the brightness correction table TB are set so that the lowest values are in the center area and the highest values are in the periphery of the imaging field of view of the imaging element 22. That is, the correction values of the brightness correction table TB are set to the reverse distribution relative to the distribution of curve L1.

The curve labeled L20 in FIG. 9 is corrected brightness distribution (curve L0) of the image obtained by imaging the reference board using the brightness correction table TB. When referring to the curve L0, it can be understood that the brightness is substantially constant within the field of view of the imaging element 22 although there are slight fluctuations due to noise. Based on this principle, the image processing part 82 corrects the brightness of each partial image G11 through G14 using the brightness correction table TB.

When the correction processing of each partial image G11 through G14 is completed, the image processing part 82 performs the combining process to combine the corrected partial images G11 through G14 and obtain the composite image G20 that includes the entire test piece TP. As described using FIG. 7, the imaging areas A1 through A4 at imaging positions P11 through P14 are set to create overlap parts Q1 through Q3. Therefore, two partial images are obtained that image the same part of the test piece TP. For example, the partial image G11 shown in FIG. 8 (A) and the partial image G12 shown in FIG. 8 (B) include the image of the reagent pad PD of the test piece TP.

The image processing part 82 combines the partial images G11 through G14 so as to obtain an image of the successive entire test piece TP and does not include the same partial images of the test piece TP. For example, the image processing part 82 performs the combining process to cutout the regions (regions R11 through R14 shown in FIG. 8 (A) through (D)) excluding areas equivalent to half the width of the overlap parts Q1 and Q2 shown in FIG. 7 from the bilateral ends of each of the partial images G11 through G14. As described using FIG. 7, however, since the width of the overlap part Q3 is greater than the width of the overlap parts Q1 and Q2, it is necessary to adjust the width by the portion to be excluded at the right end of the partial image G13 and portion to be excluded at the left end of the partial image G14.

When the combining process is completed and the composite image G20 is obtained, the image processing part 82 performs the extraction process to extract the extraction image G30 from the composite image G20. For example, a process is performed to detect the edges of the image of the test piece TP and extract the extraction image G30 after performing a Hough transform on the composite image G20 shown in FIG. 8 (E), extracting a rectangular shape representing the outer edge of the test piece TP, and rotating the composite image G20 based on the incline of the extracted rectangular shape.

When the above process is completed, the extraction image G30 that was extracted by the image processing part 82 is input to the analyzing part 83 through the controller 81 shown in FIG. 6, the degree of coloration of the reagent pad PD provided on the test piece TP is measured, and concentration analyses are performed for the sugar, protein, occult blood and the like contained in the urine. The analysis results of the analyzing part 83 are output to the controller 81, and displayed on the display part 50 or printed by the printing part 60 under the control of the controller 81.

Figure 10:
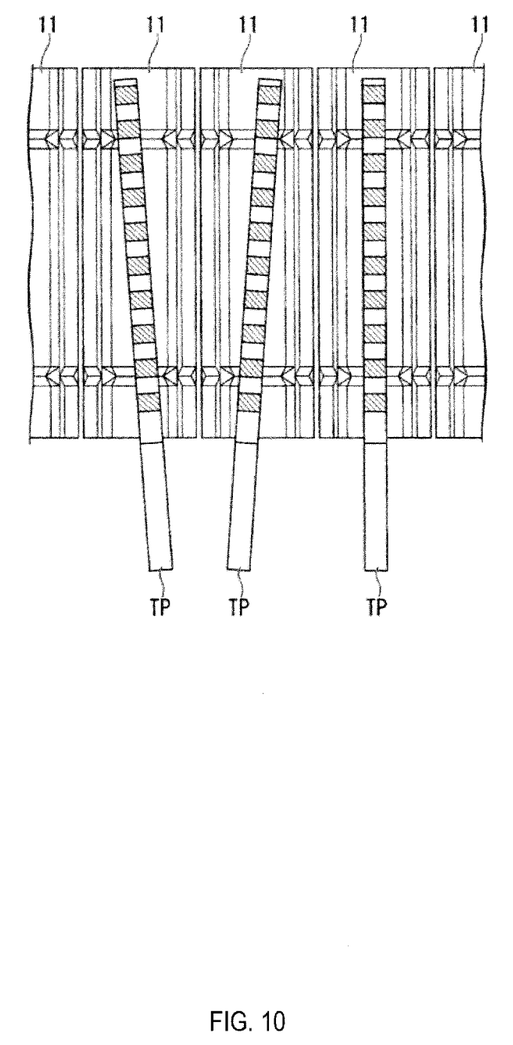
FIG. 10 shows the situation of transporting a plurality of test piece in the embodiment of the invention.

The operator also performs the work of immersing the test piece TP in the urine liquid sample, and mounting the test piece TP on the test piece holder 11 at the mounting position P1 through the mounting port OP at constant time intervals (for example, every 10 seconds). Then the test pieces TP are sequentially transported to the imaging position P2 while mounted in adjacent test piece holders 11 as shown in FIG. 10. FIG. 10 shows the situation of transporting a plurality of test piece in the embodiment of the invention.

The test pieces TP that are transported to the imaging position P2 are sequentially imaged by the imaging unit 20, and sequentially analyzed based on the acquired image. In this way analysis of the plurality of test pieces TP is performed sequentially. As shown in FIG. 10, although the test pieces TP are mounted in various states on the test piece holder 11, analysis can be performed insofar as the test piece TP is mounted on the mounting part MP of the test piece holder 11.

The embodiment described above includes a light source 21 to irradiate the test piece TP, and an imaging unit 20 provided with an imaging element 22 in which the size of the imaging area is set to image part of the test piece TP, and combines a plurality of partial images G11 through G14 obtained by the imaging element 22 images the test piece TP while changing the position of the imaging unit 20 so as to obtain a composite image G20 that includes the entire test piece TP. Therefore, the test piece analyzer 1 can be made compactly, and the test piece TP can be analyzed when obliquely mounted in the test piece holder 11.

The process of imaging a single test piece TP multiple times this way requires time compared to imaging the entire test piece TP once. However, the processing power of the test piece analyzer 1 is not adversely impacted because the time needed for imaging is set to be less than the reaction time of the next test piece TP to be imaged.

In this embodiment, the test piece TP positioned at the imaging position P2 is irradiated obliquely downward from the +X side and −X side, respectively, and brightness correction is performed using the brightness correction table relative to the partial images G11 through G14 that were acquired by the imaging element 22. In this way the brightness can be inexpensively equalized with high precision without and accompanying substantial cost increase. In the embodiment, only the image of the test piece TP is extracted as the extraction image G30 from the composite image G20. In this way the test piece TP can be analyzed without complex image processing even when the test piece TP is mounted obliquely in the test piece holder 11.

In the above embodiment, the width W1 of the mounting part MP of the test piece holder 11 is set larger than the width of the test piece TP, for example, the width W1 is set at approximately double the width of the test piece TP. Therefore, the operator can easily perform the work of mounting the test piece TP on the test piece holder 11, and the work load of the operator is reduced relative to conventional arrangements.

The test piece analyzer and test piece analyzing method of the embodiment of the invention have been described above, however, the invention is not limited to the above embodiments and may be freely modified within the scope of the claims. For example, although urine is mentioned as the liquid sample targeted for analysis in the embodiment, the liquid sample also may be a liquid other than urine (for example, blood, body fluids, other liquid).

Although an area sensor is used as the imaging element 22 in the above embodiment, a line sensor also may be used as the imaging element.

An example of correcting the brightness of the partial images G11 through G14 using the brightness correction table TB is described in the embodiment. However, the brightness correction table TB need not necessarily be used when correcting the brightness of the partial images G11 through G14, inasmuch as brightness correction also may be performed using, for example, correction functions and the like.

The above embodiment is described in terms of example in which regions (regions R11 through R14 shown in FIG. 8 (A) through (D)) required for combination from the partial images G11 through G14 are cutout, and the cutout images are connected together to obtain the composite image G20. However, the composite image G20 also may be obtained by overlaying partial images G11 through G14 similar to the imaged areas A1 through A1 shown in FIG. 7, and connecting the overlaid partial images G11 through G14.

The above embodiment has been described by way of example of performing a Hough transform relative to the composite image G20 when extracting the extraction image G30 from the composite image G20. However, a Hough transform need not necessarily be performed on the composite image G20, inasmuch as the extraction image G30 also may be extracted using another method. For example, it also is possible to extract the extraction image G30 by detecting the edges of the image of the test piece TP, and cutting out the composite image G20 along the detected edges.

Although the above embodiment describes an example of obtaining four partial images G11 through G14 by imaging the test piece TP four times, the test piece TP also may be imaged more than four times. The number of imagings of the test piece TP is roughly determined by the size of the imaging area of the imaging element 22. Therefore, the number of imagings of the test piece TP tends to be greater when a more compact test piece analyzer 1 is required.

What is claimed is:
1. A test piece analyzer comprising:
a test piece holder including a bottom plate on which a test piece including reagent pads is placed, wherein each of the bottom plate and the test strip placed on the bottom plate extends in a longitudinal direction, and the bottom plate has a width greater than a width of the test piece in a lateral direction intersecting with the longitudinal direction; and an imaging unit comprising a light source configured to irradiate the test piece placed on the bottom plate and an imaging element configured to capture a partial image of a part of the irradiated test strip, wherein the imaging element is positioned so that a width of an imaging area is greater than the width of the bottom plate in the lateral direction and a length of the imaging area is smaller than a length of the test piece in the longitudinal direction; and a processor programmed to control the imaging unit to sequentially capture partial images of the test piece along the longitudinal direction, and combine the captured partial images to generate a composite image of the test strip.

2. The test piece analyzer of claim 1, further comprising: a drive part configured to move the imaging unit along the longitudinal direction.

3. The test piece analyzer of claim 1, wherein
the light source comprises a pair of light sources respectively arranged obliquely above the bottom plate; and
the pair of light sources are respectively configured to irradiate obliquely downward on the test piece placed on the bottom plate.

4. The test piece analyzer of claim 1, wherein
the processor is programmed to correct brightness of the partial images.

5. The test piece analyzer of claim 4, further comprising
a memory storing a brightness correction table to correct irregular brightness within the imaging area of the imaging element, wherein
the processor is programmed to correct the brightness of the partial images using the brightness correction table.

6. The test piece analyzer of claim 1, wherein
the processor is programmed to extract an image of the test piece from the composite image.

7. The test piece analyzer of claim 1, wherein
the imaging unit comprises a support configured to integratedly support the imaging element and the light source.

8. The test piece analyzer of claim 1, further comprising:
a transport unit having the test piece holder, and configured to transport the test piece from a first position to a second position by moving the test piece holder along the lateral direction.

9. The test piece analyzer of claim 1, wherein
the test piece holder further comprises pair of side plates extending from both side edges of the bottom plate.

10. A test piece analyzing method for analyzing a test piece using a captured image of the test piece provided with reagent pads, the test piece analyzing method comprising:
irradiating the test piece placed on a bottom plate of a test piece holder by a light source;
sequentially capturing partial images of the test piece irradiated by the light source along a longitudinal direction of the bottom plate by an imaging element, wherein the imaging element is positioned so that a width of an imaging area is greater than a width of the bottom plate in a lateral direction intersecting with the longitudinal direction and a length of the imaging area is smaller than a length of the test piece in the longitudinal direction; and
combining the captured partial images to generate a composite image of the test strip.

11. The test piece analyzing method of claim 10, wherein
the partial images of the test piece are captured by the imaging element while changing the position of the imaging element, in the step of sequentially capturing the partial images of the test piece.

12. The test piece analyzing method of claim 10, further comprising:
correcting brightness of the partial images.

13. The test piece analyzing method of claim 1, further comprising:
extracting an image of the test piece from the composite image.

14. The test piece analyzing method of claim 10, wherein
the imaging element is moved along the longitudinal direction of the bottom plate in the step of sequentially capturing the partial images of the test piece.

15. The test piece analyzing method of claim 10, wherein
the width of the bottom plate is greater than the width of the test piece.

* * * * *